US008748088B2

(12) United States Patent
Stevenson

(10) Patent No.: US 8,748,088 B2
(45) Date of Patent: Jun. 10, 2014

(54) METHODS OF MONITORING TREATMENT EFFECTIVENESS IN HIV-INFECTED PATIENTS RECEIVEING INTENSIFIED HAART REGIMENS BY MEASURING EPISOMAL 2-LTR CIRCLES

(75) Inventor: Mario Stevenson, Miami, FL (US)

(73) Assignee: University of Massachusetts, Shrewsbury, MA (US)

(*) Notice: Subject to any disclaimer, the term of this patent is extended or adjusted under 35 U.S.C. 154(b) by 167 days.

(21) Appl. No.: 13/145,307

(22) PCT Filed: Jan. 29, 2010

(86) PCT No.: PCT/US2010/022543
§ 371 (c)(1),
(2), (4) Date: Sep. 23, 2011

(87) PCT Pub. No.: WO2010/088491
PCT Pub. Date: Aug. 5, 2010

(65) Prior Publication Data
US 2012/0034597 A1   Feb. 9, 2012

Related U.S. Application Data

(60) Provisional application No. 61/148,687, filed on Jan. 30, 2009.

(51) Int. Cl.
*C12Q 1/70* (2006.01)
*A61K 39/21* (2006.01)
*C07H 21/04* (2006.01)

(52) U.S. Cl.
USPC .................. 435/5; 424/208.1; 536/23.72

(58) Field of Classification Search
None
See application file for complete search history.

(56) References Cited

U.S. PATENT DOCUMENTS

| 6,797,464 B2 | 9/2004 | Stevenson et al. |
| 7,232,657 B2 | 6/2007 | Stevenson et al. |
| 2002/0048584 A1 | 4/2002 | Pomerantz |
| 2005/0064393 A1 | 3/2005 | Stevenson |

OTHER PUBLICATIONS

Buzon, M. J., et al., Apr. 2010, HIV-1 replication and immune dynamics are affected by raltegravir intensification of HAART-suppressed subjects, Nat. Med. 16(4):460-466.*
Sharkey, M., et al., Apr. 2005, In vivo evidence for instability of episomal human immunodeficiencyvirus type 1 cDNA, J. Virol. 79(8):5203-5210.*

(Continued)

*Primary Examiner* — Jeffrey Parkin
(74) *Attorney, Agent, or Firm* — Fish & Richardson P.C.

(57) ABSTRACT

Provided herein are methods for detecting the presence of replication-competent HIV-1 virus in a subject who is being treated with an intensified highly active anti-retroviral therapy (HAART) regimen. These methods comprise selecting a subject who is being treated with an intensified HAART regimen including an integration inhibitor; obtaining a sample, e.g., a blood sample, from a subject; specifically amplifying a segment spanning two-long terminal repeat (2-LTR) junction of 2-LTR circles using PCR to determine the level of 2-LTR circles in the sample; and determining the presence of replication competent virus based on the level of 2-LTR circles in the sample. These methods can also be used to monitor an intensified HAART regimen by obtaining samples from the same subject at different time points during the HAART treatment, and comparing levels of the 2-LTR circles in those samples.

20 Claims, 9 Drawing Sheets

(56) References Cited

OTHER PUBLICATIONS

Kolber, M. A., et al., 2008, Intensification of a suppressive HAART regimen increases CD4 counts and decreases CD8+ T-cell activation, Clin. Immunol. 126:315-321.*

Hughes, A., et al., 2008, New treatment options for HIV salvage patients: an overview of second generation PIs, NNRTIs, integrase inhibitors and CCR5 antagonists, J. Infection 57:1-10.*

Bailey et al., "Residual human immunodeficiency virus type 1 viremia in some patients on antiretroviral therapy is dominated by a small number of invariant clones rarely found in circulating CD4+ T cells," J. Virol., 80:6441-6457 (2006).

Brenchley et al., "Microbial translocation is a cause of systemic immune activation in chronic HIV infection," Nat. Med., 12:1365-1371 (2006).

Brussel and Sonigo, "Analysis of early human immunodeficiency virus type 1 DNA synthesis by use of a new sensitive assay for quantifying integrated provirus," J. Virol., 77:10119-10124 (2003).

Chun et al., "HIV-infected individuals receiving effective antiviral therapy for extended periods of time continually replenish their viral reservoir," J. Clin. Invest., 115:325-3255 (2005).

Chun et al., "Decay of the HIV reservoir in patients receiving antiretroviral therapy for extended periods: implications for eradication of virus," J. Infect Dis., 195:1762-1764 (2007).

Chun et al., "Early establishment of a pool of latently infected, resting CD4(+) T cells during primary HIV-1 infection," Proc. Natl. Acad. Sci. USA, 95:8869-8873 (1998).

Clayman et al., "Circular forms of DNA synthesized by *Rous sarcoma* virus in vitro," Science, 206:582-584 (1979).

Garrido et al., "Evaluation of Eight Different Bioinformatics Tools to Predict Viral Tropism in Different Human Immunodeficiency Virus Type 1 Subtypes," Journal of Clinical Microbiology, 46(3):887-891 (2008).

Gulick et al., "Maraviroc for previously treated patients with R5 HIV-1 infection," N. Engl. J. Med., 359(14):1429-1441 (2008).

Gunthard et al., "Evolution of envelope sequences of human immunodeficiency virus type 1 in cellular reservoirs in the setting of potent antiviral therapy," J. Virol., 73:9404-9412 (1999).

Hezareh, "Prostratin as a new therapeutic agent targeting HIV viral reservoirs," Drug News Perspect., 18(8):496-500 (2005).

Hunt et al., "T cell activation is associated with lower CD4+ T cell gains in human immunodeficiency virus-infected patients with sustained viral suppression during antiretroviral therapy," J. Infect. Dis., 187:1534-1543 (2003).

International Search Report as issued in PCT/US2010/022543 on Oct. 12, 2010.

Jensen et al., "Improved Coreceptor Usage Prediction and Genotypic Monitoring of R5-to-X4 Transition by Motif Analysis of Human Immunodeficiency Virus Type 1 env V3 Loop Sequences," Journal of Virology, 77(24):13376-13388 (2003).

Jiang et al., "Plasma levels of bacterial DNA correlate with immune activation and the magnitude of immune restoration in persons with antiretroviral-treated HIV infection," J. Infect. Dis., 199:1177-1185 (2009).

Joos et al., "HIV rebounds from latently infected cells, rather than from continuing low-level replication," Proc. Natl. Acad. Sci. USA, 105:15725-16730 (2008).

Jurrians et al., "Analysis of human immunodeficiency virus type 1 LTR-LTR junctions in peripheral blood mononuclear cells of infected individuals," J. Gen. Virol., 73:1537-1541 (1992).

Kieffer et al., "Genotypic analysis of HIV-1 drug resistance at the limit of detection: virus production without evolution in treated adults with undetectable HIV loads," J. Infect. Dis., 189:1452-1465 (2004).

Kolber et al., "Intensification of a suppressive HAART regimen increases CD4 counts and decreases CD8+ T-cell activation," Clin. Immunol., 126:315-321 (2008).

Martinez et al., "Human immunodeficiency virus type 1 genetic evolution in patients with prolonged suppression of plasma viremia," Virology, 256:180-187 (1999).

Martinez-Picado et al., "Viral evolution during structured treatment interruptions in chronically human immunodeficiency virus-infected individuals," J. Virol., 76:12344-12348 (2002).

Middleton et al., "Inhibition of human immunodeficiency virus type I integrase by naphthamidines and 2-aminobenzimidazoles," Antiviral Res., 64:35-45 (2004).

Palmer et al., "New real-time reverse transcriptase-initiated PCR assay with single-copy sensitivity for human immunodeficiency virus type 1 RNA in plasma," J. Clin. Microbiol., 41:4531-4536 (2003).

Palmer et al., "Low-level viremia persists for at least 7 years in patients on suppressive antiretroviral therapy," Proc. Natl. Acad. Sci. USA, 105:3879-3884 (2008).

Panther et al., "Unintegrated circular HIV-1 DNA in the peripheral mononuclear cells of HIV-1-infected subjects: association with high levels of plasma HIV-1 RNA, rapid decline in CD4 count, and clinical progression to AIDS," J. Acquir. Immune. Defic. Syndr. Hum. Retro., 17:303-313 (1998).

Parera et al., "Lack of evidence for protease evolution in HIV-1-infected patients after 2 years of successful highly active antiretroviral therapy," J. Infect. Dis., 189:1444-1451 (2004).

Pauza et al., "2-LTR circular viral DNA as a marker for human immunodeficiency virus type 1 infection in vivo," Virology, 205:470-478 (1984).

Perelson et al., "Decay characteristics of HIV-1-infected compartments during combination therapy," Nature, 387:188-191 (1997).

Peterson et al., "Treatment implications of the latent reservoir for HIV-1," Adv. Pharmacol., 55:411-425 (2007).

Poveda et al., "Correlation between a phenotypic assay and three bioinformatic tools for determining HIV co-receptor use," AIDS, 21(11):1487-1490 (2007).

Ramratnam et al., "The decay of the latent reservoir of replication-competent HIV-1 is inversely correlated with the extent of residual viral replication during prolonged anti-retroviral therapy," Nat. Med., 6:82-85 (2000).

Sedaghat et al., "Limits on replenishment of the resting CD4+ T cell reservoir for HIV in patients on HAART," PLos Pathog., 3:e122 (2007).

Shank et al., "Virus-Specific DNA in the Cytoplasm of *Avian sarcoma* Virus-Infected Cells is a Precursor to Covalently Closed Circular Viral DNA in the Nucleus," J. Virol., 25:104-114 (1978).

Sharkey et al., "In vivo evidence for instability of episomal human immunodeficiency virus type 1 cDNA," J. Virol., 79:5203-5210 (2005).

Skrabal et al., "Determining Human Immunodeficiency Virus Coreceptor Use in a Clinical Setting: Degree of Correlation between Two Phenotypic Assays and a Bioinformatic Model," Journal of Clinical Microbiology, 45(2):279-284 (2007).

Stevenson et al., "HIV-1 replication is controlled at the level of T cell activation and proviral integration," EMBO J., 9:1551-1560 (1990).

Stevenson et al., "Integration is not necessary for expression of human immunodeficiency virus type 1 protein products," J. Virol., 64:2421-2425 (1990).

Svarovskaia et al., "Azido-containing diketo acid derivatives inhibit human immunodeficiency virus type 1 integrase in vivo and influence the frequency of deletions at two-long-terminal-repeat-circle junctions," J. Virol., 78:3210-3222 (2004).

Teo et al., "Reliable and reproducible LightCycler qPCR for HIV-1 DNA 2-LTR circles," Journal of Immunological Methods, 270:109-118 (2002).

Scott L. Butler et al., "Human Immunodeficiency Virus cDNA Metabolism: Notable Stability of Two-Long Terminal Repeat Circles", *Journal of Virology*, vol. 76, No. 8, pp. 3739-3747 (Apr. 2002).

John M. Murray et al., "Integrated HIV DNA accumulates prior to treatment while episomal HIV DNA records ongoing transmission afterwards", *AIDS*, vol. 26, No. 5, pp. 543-550 (2012).

Matthew J. Pace et al., "HIV e-long terminal repeat circular DNA is stable in primary CD4+T Cells", *Virology* 441, pp. 18-21 (2013).

Theodore C. Pierson et al., "Intrinsic Stability of Episomal Circles Formed during Human Immunodeficiency Virus Type 1 Replication", *Journal of Virology*, vol. 76, No. 8, pp. 4138-4144 (Apr. 2002).

Weijun Zhu et al., "Rapid Turnover of 2-LTR HIV-1 DNA during Early Stage of Highly Active Antiretroviral Therapy", *PLoS One*, vol. 6, Issue 6, pp. 1-10 (Jun. 2011).

* cited by examiner

METHODS OF MONITORING TREATMENT EFFECTIVENESS IN HIV-INFECTED PATIENTS RECEIVEING INTENSIFIED HAART REGIMENS BY MEASURING EPISOMAL 2-LTR CIRCLES

CLAIM OF PRIORITY

This application is a U.S. national stage application under 35 USC §371 of International Application Number PCT/US2010/022543, filed on Jan. 29, 2010, which claims the benefit of U.S. Provisional Patent Application Ser. No. 61/148,687, filed on Jan. 30, 2009, the entire contents of which are hereby incorporated by reference.

TECHNICAL FIELD

This invention relates to methods of monitoring the efficacy of treatment in aviremic (Human Immunodeficiency) Virus HIV-infected patients.

BACKGROUND

Present treatment modalities (i.e., highly active anti-retroviral therapies or HAART) for patients diagnosed with HIV have progressed to the extent that many patients have extremely low or undetectable levels of virus in their plasma, i.e., they are aviremic. However, in most cases, once the patient stops taking their medications (takes a "drug holiday"), the virus rebounds and a resurgence of viral replication is seen. This indicates that, while there may be no detectable levels of virus in the plasma in well-controlled patients, a reservoir of replication-competent virus still exists. Furthermore, even in patients who are well-suppressed, i.e., who have fewer than 40 or 50 copies/mL of plasma viral RNA, episomal infection intermediates, 2-LTR circles, can usually be detected, indicating ongoing cryptic or covert replication. See, e.g., U.S. Pat. Nos. 7,232,657 and 6,797,464; and U.S. Pat. Pub. No. 2005-0064393.

New treatment methods have been developed, referred to as "intensified HAART," in which newly-developed drugs, e.g., drugs targeting the viral receptors or the viral integration process, are added to a HAART regimen in an attempt to achieve complete viral eradication.

SUMMARY

Figure 1A:
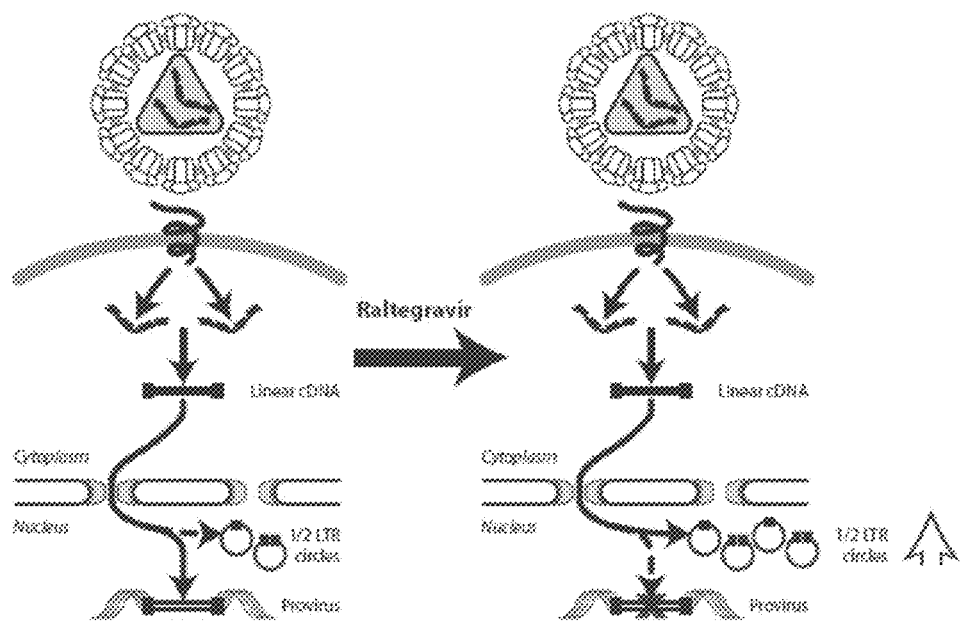
FIG. 1A is a schematic illustration of a theoretical mechanism by which Raltegravir blocks integration to promote episome formation. In the presence of raltegravir, integration of linear viral cDNA is blocked and subsequently is circularized by host DNA repair enzymes to form episomes containing 2 copies of the viral long terminal repeat (2-LTR circles) or undergoes recombination to form a 1-LTR circle. Therefore, an increase in episomal cDNA occurs when active replication is inhibited by raltegravir.

As described herein, subjects who are being treated with intensified HAART still have detectable levels of 2-LTR circles in their blood; levels of 2-LTR circles can be used to monitor the effectiveness of the treatment.

Thus, the present invention features methods of monitoring or determining the efficacy of a treatment, the method comprising selecting a subject who is being treated with intensified HAART, obtaining a sample comprising blood, e.g., blood cells, e.g., peripheral blood mononuclear cells (PBMCs), and determining a level of 2-LTR circles in the sample. The level of 2-LTR circles in the sample indicates whether or how effective the treatment is. In some embodiments, the methods further include obtaining a second sample from the same subject at a later time, e.g., at least about one, two, three, four, five, or six months later, determining a second level of 2-LTR circles in the second sample, and comparing the first and second level of 2-LTR circles. A decrease in the levels, e.g., a decrease in 2-LTR circles over a 6 month period, indicates that the treatment is effective.

In some embodiments, the methods include obtaining a baseline level of 2-LTR circles in a subject who is being treated with standard HAART; adding an intensification agent to the HAART treatment; and obtaining a treatment level of 2-LTR circles in the subject. In some embodiments, e.g., wherein the intensification agent is an integration inhibitor, and the treatment level is obtained about two weeks after addition of the intensification agent, the presence of a treatment level of 2-LTR circles that is greater than the baseline level indicates that the intensification is effective. This increase at 2 weeks is due to the type of inhibitor used (i.e., an integration inhibitor). It is reasonable to expect that the 2-LTR levels will subsequently drop to below baseline levels.

In some embodiments, the methods include determining that the subject has no detectable plasma levels of viral RNA, e.g. determining that the subject has fewer than about 50 copies/ml plasma, e.g., for at least a desired period of time, e.g., at least two weeks or more, e.g., at least one, two, three, four, five, six, twelve, or more months. Such a determination can be made using methods known in the art or described herein, and can include reviewing the subject's medical records to confirm that the subject has no detectable plasma viral RNA.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Highly active antiretroviral therapy (HAART) is able to sustain suppression of plasma viremia below the limit of detection of standard assays (Perelson et al., Nature 387, 188-191 (1997)). However, viremia rapidly resumes if therapy is interrupted suggesting that some viral reservoirs persist in the face of HAART. HIV-1 persistence in HAART has been attributed to the presence of a long-lived reservoir of latently infected, memory CD4+ T cells, a model that is supported by the presence of replication-competent virus in peripheral blood lymphocytes and by the lack of evolution in viral cDNA (Bailey et al., J Virol 80, 6441-6457 (2006); Joos et al., Proc Natl Acad Sci USA 105, 16725-16730 (2008); Kieffer et al., J Infect Dis 189, 1452-1465 (2004); Parera et al., J Infect Dis 189, 1444-1451 (2004); Sedaghat et al., PLoS Pathog 3, e122 (2007)). According to this model, therapy intensification should have no impact on the reservoir that persists in HAART (Peterson et al., Adv Pharmacol 55, 411-425 (2007)). While it is generally believed that HAART stops active infection, elevated levels of immune activation/inflammation persist in HAART-suppressed patients (Jiang et al., J. Infect Dis 199, 1177-1185 (2009)). This, and additional studies (Chun et al., Proc Natl Acad Sci USA 95, 8869-8873 (1998); Chun et al., J Infect Dis 195, 1762-1764 (2007); Chun et al., J Clin Invest 115, 3250-3255 (2005); Gunthard et al., J Virol 73, 9404-9412 (1999); Martinez et al., Virology 256, 180-187 (1999); Martinez-Picado et al., J Virol 76, 12344-12348 (2002); Ramratnam et al., Nat Med 6, 82-85 (2000); Sharkey et al., J Virol 79, 5203-5210 (2005)), suggest that low level, active or "cryptic" replication may persist in the face of suppressive HAART. Residual low level viremia has been detected with ultrasensitive assays that are able to measure down to one copy RNA/ml plasma (Palmer et al., J Clin Microbiol 41, 4531-4536 (2003); Palmer et al., Proc Natl Acad Sci USA 105, 3879-3884 (2008)). Whether residual viremia reflects viral replication or the production of virus from stable reservoirs without additional cycles of replication, is unknown.

New classes of antiretroviral agents against viral integrase and CCR5 increase the treatment options for HIV-1 infected individuals but also serve as tools with which to assess the viral reservoirs that persist in HAART suppressed patients. Raltegravir is a first-in-class integrase strand transfer inhibitor that has recently been approved for the treatment of HIV-1 infection. In the presence of raltegravir, integration of linear viral cDNA is blocked and subsequently is circularized by host DNA repair enzymes to form episomes containing two copies of the viral long terminal repeat (2-LTR circles) or undergoes recombination to form a 1-LTR circle. Therefore, an increase in episomal cDNA occurs when active replication is inhibited by raltegravir (Middleton et al., Antiviral Res 64, 35-45 (2004); Svarovskaia et al., J Virol 78, 3210-3222 (2004)) (FIG. 1A). The present methods exploit this unique relationship between episomes and raltegravir to reveal active replication in patients on HAART.

Subjects

The subjects who are candidates for the methods described herein are those whose disease (as measured by viral load) has been well-suppressed on HAART, e.g., patients who have had undetectable (fewer than 40 or 50 copies/mL) plasma viral RNA for at least a month, e.g., for at least six months, nine month, or a year.

Treatment Regimens

A number of HAART regimens are presently used; exemplary regimes can include combinations of Nucleoside Reverse Transcriptase Inhibitors (NRTIs), Protease Inhibitors (PI), and/or non-nucleoside reverse transcriptase inhibitors (NNRTIs). In some embodiments, the subject is being treated with a regimen that includes 2 NRTI plus an NNRTI and/or a PI. In the present methods, the subject's treatment is intensified by the addition of an additional drug or drugs that inhibits entry of the virus into cells (entry inhibitors) and/or that targets viral integration into genomic DNA (integration inhibitors).

Dosages, specific formulations, and routes of administration of HIV antiviral drugs are known in the art. See, e.g., *Physicians' Desk Reference*, 63rd edition (Medical Economics Company, Montvale, N.J., 2009); Panel on Antiretroviral Guidelines for Adult and Adolescents, "Guidelines for the use of antiretroviral agents in HIV-1-infected adults and adolescents." Department of Health and Human Services. Nov. 3, 2008; pp 1-139 (available at aidsinfo.nih.gov/ContentFiles/AdultandAdolescentGL.pdf); and Kuritzkes et al. (1999, AIDS 13:685-694).

NRTIs

NRTIs are the nucleoside and nucleotide analogs, which replace the normal endogenous nucleotides/nucleosides, preventing the reverse transcriptase from transcribing viral RNA. Exemplary NRTIs are listed in Table A.

TABLE A

Nucleoside Reverse Transcriptase Inhibitors (NRTIs)

| Brand Name | Generic Name | Pharmaceutical Company |
|---|---|---|
| COMBIVIR | zidovudine + lamivudine | GlaxoSmithKline |
| EMTRIVA | emtricitabine | Gilead Sciences |
| EPIVIR | lamivudine | GlaxoSmithKline |
| EPZICOM | abacavir + lamivudine | GlaxoSmithKline |
| RETROVIR | zidovudine | GlaxoSmithKline |
| TRIZIVIR | abacavir + zidovudine + lamivudine | GlaxoSmithKline |
| TRUVADA | tenofovir DF + emtricitabine | Gilead Sciences |
| VIDEX & VIDEX EC | didanosine | Bristol-Myers Squibb |
| VIREAD | tenofovir disoproxil fumarate (DF) | Gilead Sciences |
| ZERIT | stavudine | Bristol-Myers Squibb |
| ZIAGEN | abacavir | GlaxoSmithKline |
| RACIVIR | | Pharmasset |
| | amdoxovir | RFS Pharma |
| | apricitabine | Avexa Limited |
| | elvucitabine | Achillion Pharmaceuticals |

PIs

PIs inhibit the activity of the HIV protease, preventing the production of functional viral particles. Exemplary PIs are listed in Table B.

TABLE B

Protease Inhibitors (PIs)

| Brand Name | Generic Name | Pharmaceutical Company |
|---|---|---|
| AGENERASE | amprenavir | GlaxoSmithKline and Vertex |
| APTIVUS | tipranavir | Boehringer Ingelheim |
| CRIXIVAN | indinavir | Merck & Co |
| INVIRASE | saquinavir | Hoffmann-La Roche |
| KALETRA | lopinavir + ritonavir | Abbott Laboratories |
| LEXIVA | fosamprenavir | GlaxoSmithKline |
| NORVIR | ritonavir | Abbott Laboratories |
| PREZISTA | darunavir | Tibotec |
| REYATAZ | atazanavir | Bristol-Myers Squibb |
| VIRACEPT | nelfinavir | Pfizer |

NNRTIs

NNRTIs bind to reverse transcriptases and prevent the transcription of viral RNA. Exemplary NNRTIs are listed in Table C.

TABLE C

Non-Nucleoside Reverse Transcriptase Inhibitors (NNRTIs)

| Brand Name | Generic Name | Pharmaceutical Company |
|---|---|---|
| INTELENCE | etravirine | Tibotec |
| RESCRIPTOR | delavirdine | Pfizer |
| SUSTIVA | efavirenz | Bristol-Myers Squibb |
| VIRAMUNE | nevirapine | Boehringer Ingelheim |
| | rilpivirine | Tibotec |

Intensification Therapies—Integration Inhibitors and Entry Inhibitors

Drugs useful for intensification include integration inhibitors and entry inhibitors. A number of integration inhibitors are known in the art, including raltegravir (Merck & Co), elvitegravir (Gilead Sciences), Globoidnan A, MK-2048 (Merck & Co), GSK-744 (GlaxoSmithKline), and GSK-572 (GlaxoSmithKline). Beta diketo acid inhibitors can also be used, e.g., 5-aryl(heteroaryl)-isoxazole-3-carboxylic acid biological isosteric analogues of β-diketo acid (Sechi et al., Antiviral chemistry & chemotherapy, 2005, 16(1):41-61); bifunctional quinolonyl diketo acid derivatives (Di Santo et al., J Med Chem. 2006 Mar. 23; 49(6): 1939-1945); and pyrroloquinoline and naphthyridine carboxamide (e.g., as described in Louizidou et al., Bioorg Med Chem. 2009, 17(13):4806-18 and Marchand et al., Curr Top Med Chem. 2009; 9(10):1016-37).

Entry inhibitors generally target the gp120 or gp41 proteins on HIV's surface, or the CD4 protein, or CCR5 or CXCR4 receptors on a CD4 cell's surface, e.g., enfuvirtide (Trimeris and Hoffmann-La Roche, targets gp41); maraviroc (Pfizer. targets CCR5); vicriviroc (Schering-Plough Corporation, targets CCR5); PRO 140 (Progenics Pharmaceuticals, targets the CD4 protein); and TNX-355 (Tanox, Inc., targets the CD4 protein).

In some embodiments, the intensification includes administration of an integration inhibitor, e.g., raltegravir.

Sample Preparation

A variety of biological samples can be analyzed by the methods of the invention, including blood and solid-tissue biopsies (e.g., a lymph node biopsy). For example, blood can be collected from an HIV-positive individual undergoing combination therapy. Peripheral blood mononuclear cells (PBMC) are isolated by standard FICOLL™-based isolation procedures. The PBMC are then lysed and the total or extrachromosomal DNA isolated.

Total cellular DNA can be extracted by lysing the PBMC in detergent, digesting the cellular protein, and precipitating the DNA (Pauza et al., Virology, 205:470-478, 1984; and Panther et al., J. Acquir. Immune. Defic. Syndr. Hum. Retro. 17:303-313, 1998). Extrachromosomal DNA can be isolated by methods known in the art, including standard alkaline lysis, Hirt extraction, or guanidinium thiocyanate precipitation (Jurrians et al., J. Gen. Virol. 73:1537-1541, 1992; Stevenson et al., J. Virol. 64:2421-2425, 1990; and Sambrook et al., eds., *Molecular Cloning: A Laboratory Manual. 2nd, ed., Cold Spring Harbor Laboratory*, Cold Spring Harbor Laboratory Press, Cold Spring Harbor, N.Y., 1989).

Standard alkaline lysis technique, used for isolating plasmid DNA from bacteria, can also be used according to the invention to isolate 2-LTR circles from mammalian cells. The Spin Miniprep Kit available from Qiagen (Cat. No. 27104) is, for example, useful for this purpose. The methods of the invention include the use of this technique to isolate and purify 2-LTR circle DNA.

When possible, extrachromosomal DNA, instead of total DNA, should be isolated since the number of target 2-LTR circles per microgram of extrachromosomal DNA is expected to be greater than the number of 2-LTR circles per microgram of total cellular DNA.

2-LTR Circles and Methods of Detection

In vitro studies of retroviruses have shown that the first evidence of reverse transcription is unintegrated viral DNA appearing in the cytoplasm, which is transported to the nucleus within hours after infection of a cell (Shank et al., J. Virol. 25:104-114, 1978; Clayman et al., Science, 206:582-584, 1979; and Stevenson et al., EMBO J., 9:1551-1560, 1990). In the case of HIV-1, this unintegrated DNA exists in several forms, including incompletely or completely reverse-transcribed linear DNA, circular DNA containing one LTR, and circular DNA containing two LTRs (2-LTR circles). 2-LTR circles are identical to integrated proviruses, except that the ends of the LTR are joined in a head-to-tail fashion via a covalent linkage.

PCR can be used to specifically amplify a small segment (a few hundred base pairs) spanning the 2-LTR junction. The PCR is specific for 2-LTR circles, since no proviruses, single LTR circles, or other incomplete viral reverse transcription products will be amplified. Methods of detecting and/or quantifying 2-LTR circles are described herein and in the art. See, e.g., U.S. Pat. Nos. 7,232,657 and 6,797,464; and U.S. Pat. Pub. No. 2005-0064393.

For example, 2-LTR circles can be detected using known techniques, including those that do not require nucleic acid amplification, such as Southern blotting. The DNA sample obtained as described herein can be hybridized with 2-LTR circle-specific probes that are directly or indirectly labeled with chromogenic, radioactive, fluorescent, or luminescent labels.

Where amplification of the 2-LTR circles is desired, e.g., before a detection step, the 2-LTR circles can be amplified by any method well known in the art. These methods include polymerase chain reaction (PCR; U.S. Pat. Nos. 4,683,195 and 4,683,202) and variants thereof. Another suitable nucleic acid amplification method is ligation chain reaction (LCR) or variants thereof (Landegran et al., Science, 241:1077-1080, 1988; and Nakazawa et al., Proc. Natl. Acad. Sci. USA, 91:360-364, 1994). Methods for performing quantitative PCR using 2 LTR-specific primers is described in Stevenson et al., J. Virol. 64:2421-2425 (1990).

Other amplification methods include: self-sustained sequence replication (Guatelli et al., Proc. Natl. Acad. Sci. USA, 87:1874-1878, 1990), transcriptional amplification system (Kwoh, et al., Proc. Natl. Acad. Sci. USA, 86:1173-1177, 1989), and Q-Beta Replicase (Lizardi et al., Bio/Technology, 6:1197, 1988).

However the 2-LTR circles are detected, a threshold level of 2-LTR circles per million cells is useful to define meaningful numbers of the circles. If the assay is capable of single-molecule sensitivity, a base threshold can be established at one circle per million PBMC. This threshold is appropriate when determining whether eradication of HIV has been achieved in a patient. Whenever a patient tests above this threshold, the patient is said to exhibit active viral infection. Whenever a patient tests below the threshold, the patient is said to have undetectable levels of infection and may be a candidate for removal from antiviral therapy. In other contexts, such as when the level of 2-LTR circles is used to determine the efficacy of any antiviral regime, thresholds above one per million PBMC can be appropriate (e.g., 10, 50, 100, or 250 circles/$10^6$ PBMC).

Any of the above methods can be combined in a method of the invention to achieve suitable 2-LTR detection efficiencies.

Various assays have been developed to detect HIV viral RNA in plasma. A common HIV-1 detection assay utilizes quantitative polymerase chain reaction (PCR) as a means to amplify and detect viral RNA present in patient plasma. For example, plasma viral RNA in a sample can be measured using the AMPLICOR® HIV Monitor Test kit (Roche Molecular Systems, Inc., Branchburg, N.J.), employing HIV-1-specific quantitative PCR, following manufacturer's directions. The threshold of detection for this standard HIV-1 RNA detection assay is about 40-50 viral RNA molecules per milliliter of plasma.

EXAMPLES

The invention is further described in the following examples, which do not limit the scope of the invention described in the claims.

Example 1

A total of 69 patients with undetectable plasma viremia (viral load <50 HIV-1 RNA copies/ml) for at least one year were included in this study. All patients were on a suppressive HAART regimen that included 2 nucleoside reverse transcriptase inhibitors, and either a protease inhibitor or a non-nucleoside reverse transcriptase inhibitor. A total of 45 patients were randomized to intensify their HAART with the integrase inhibitor raltegravir for 12 weeks, and 24 patients were included as a control arm. One patient in the control group was lost to follow-up before study initiation. A second patient also in this group, who had two consecutive viral load measurements at weeks 12 and 24 (90 and 63 HIV-1 copies/mL respectively), was excluded for further analysis.

The samples included in this study were drawn from HIV-1 infected patients who were longitudinally monitored for up to 12 weeks. Intensified patients (n=45) were antiretroviral-experienced and had been exposed to a median of 6.7 antiretroviral drugs with a median of 4.4 NRTIs, 1.1 NNRTIs, and 1.1 PIs while none had received integrase inhibitors. The median time of the suppressive antiretroviral combination regimens was 5.0 years. Patient characteristics are summarized in Table 1, below. Non-intensified patients (n=22) were antiretroviral-experienced and had been exposed to a median of 6.9 antiretroviral drugs with a median of 4.4 NRTIs, 1.0 NNRTIs, and 1.5 PIs while none had received integrase inhibitors. The median time of the suppressive antiretroviral combination regimens was 4.5 years.

TABLE 1

Baseline characteristics between the 2-LTR− and 2-LTR+ subgroups

|  | Intensification n = 45 | | p-value |
|---|---|---|---|
|  | 2LTR−<br>n = 32 | 2LTR+<br>n = 13 | between<br>groups[a] |
| Age, (years), Mean ± SD | 47.6 ± 9.2 | 43.7 ± 7.4 | 0.633 |
| Females (%)[b] | 18.7 | 0 | 0.16 |
| ART | | | |
| PI-containing regimen at intensification, n (%)[b] | 6 (18.7) | 8 (61.5) | 0.011 |
| Number of exposed ART drugs, Mean ± SD | 7.1 ± 0.5 | 6.8 ± 0.7 | 0.747 |
| Previous salvage regimens, n (%)[b] | 8 (25) | 2 (15) | 0.710 |
| Pre-HAART Therapy, n (%)[b] | 10 (31) | 3 (23) | 1 |

TABLE 1-continued

Baseline characteristics between the 2-LTR− and 2-LTR+ subgroups

| | Intensification n = 45 | | p-value |
|---|---|---|---|
| | 2LTR−<br>n = 32 | 2LTR+<br>n = 13 | between<br>groups[a] |
| Time from diagnosis, (years), Mean ± SD | 12.3 ± 5.1 | 10.1 ± 6.1 | 0.249 |
| Time with suppressive ART, (years), Mean ± SD | 5.2 ± 2.9 | 3.5 ± 2.5 | 0.075 |
| Viral load (standard assay copies/mL) | <50 | <50 | 1 |
| CD4+ T cell, Absolute (cell/mm$^3$), Median [IQR] | 532 [434-746] | 520 [434-803] | 0.802 |
| CD8+ T cell, Absolute (cell/mm$^3$), Median [IQR] | 642 [476-867] | 732 [450-962] | 0.831 |
| Total HIV-1 DNA, (copies/10$^6$ PBMCs), Median [IQR] | 9.4 [2.6-36.6] | 22.6 [8.4-55.0] | 0.278 |
| Integrated HIV-1 DNA, (copies/10$^6$ PBMCs), Median [IQR] | 0 [0-7.4] | 0.04 [0-8.9] | 0.856 |
| Ultrasensitive Viral Load[c], (SCA, copies/mL), Median [IQR] | 0.6 [0.6-0.6] | 0.5 [0.4-0.5] | 0.353 |
| Soluble CD14, (μg/mL), Median [IQR] | 7.5 [6.3-8.6] | 8.9 [7.3-10.5] | 0.064 |

PI, protease inhibitors;
ART, antiretroviral therapy;
SCA, Single copy assay;
Viral load (copies RNA/ml plasma);
[a]p-value between groups: U Mann Whitney test;
[b]Pearson's chi square;
[c]Peto-Prentice test;
PI were lopinavir or atazanavir, and
NNRTI were efavirenz or nevirapine.

Figure 1B:
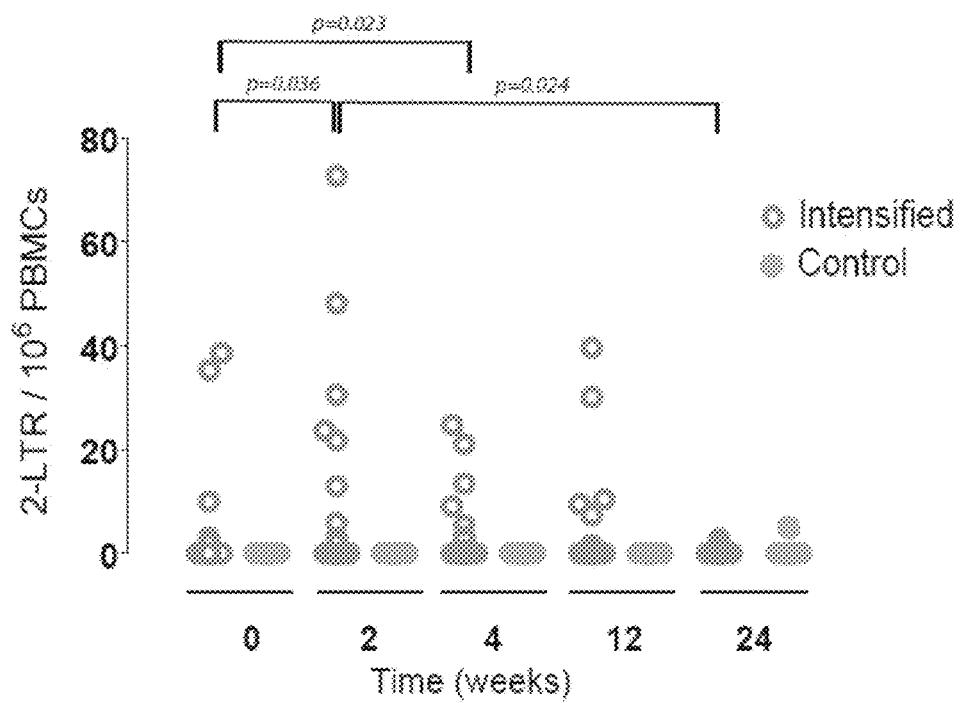
FIG. 1B is a dot graph showing changes in episomal HIV-1 DNA (2-LTR circles) between groups during the study period. Extrachromosomal DNA was extracted from $60 \times 10^6$ PBMCs at weeks 0, 2, 4 and 12 after initiation of the study and Real-Time PCR used to quantitate 2-LTR circles. Open circles represent the intensified arm (n=45) while the control arm is represented by filled circles (n=22).
Figure 1C:
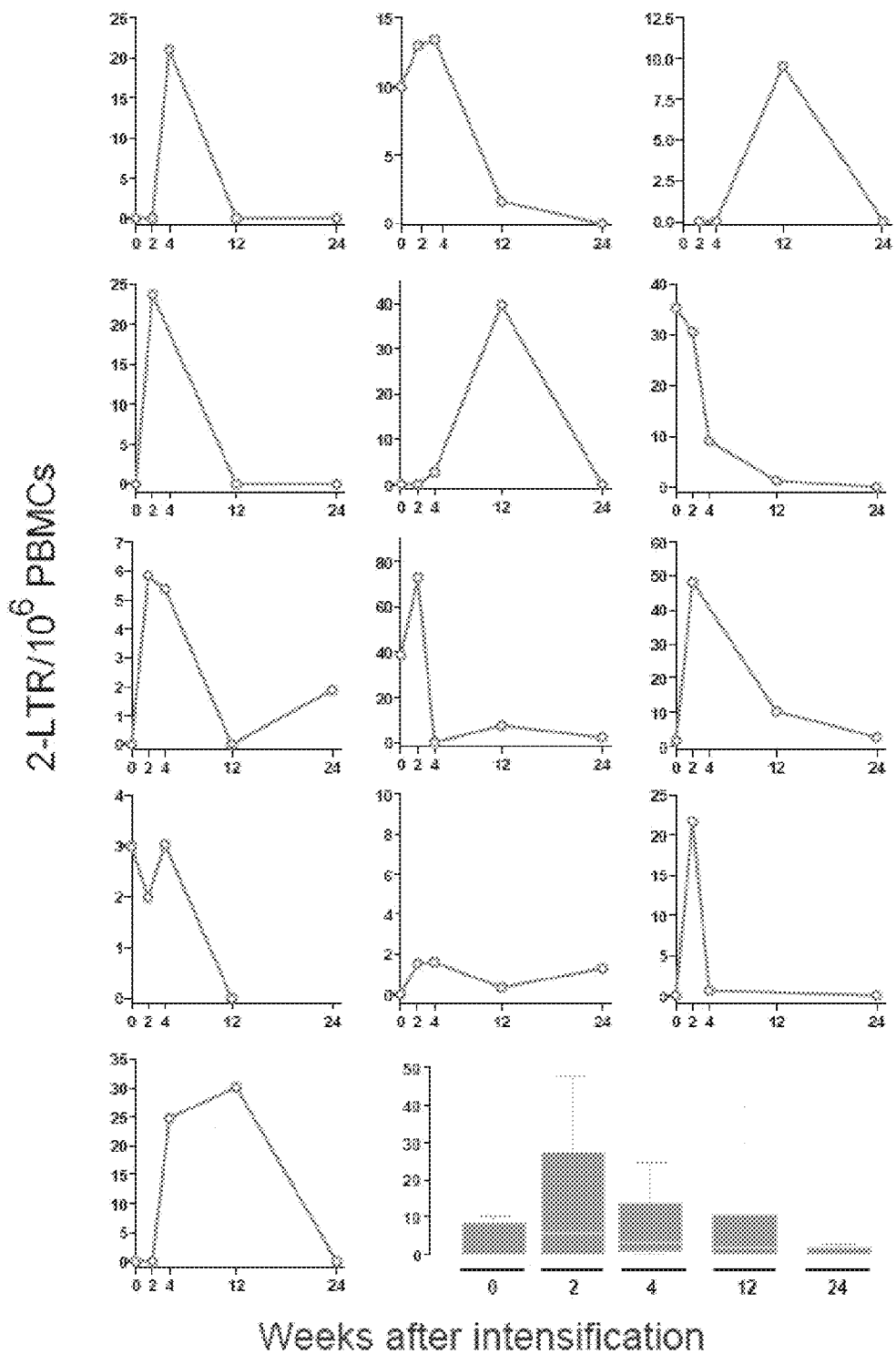
FIG. 1C is a set of thirteen line graphs, and a bar graph, showing changes in the amount of detectable episomal HIV-1 DNA (2-LTR circles, n=13) after therapy intensification with raltegravir in 13 exemplary subjects. The bar graph shows the cumulative data. P values (Peto-Prentice-Wilcoxon test) are indicated. Data are median, 25 and 75 percentiles.
Figure 1D:
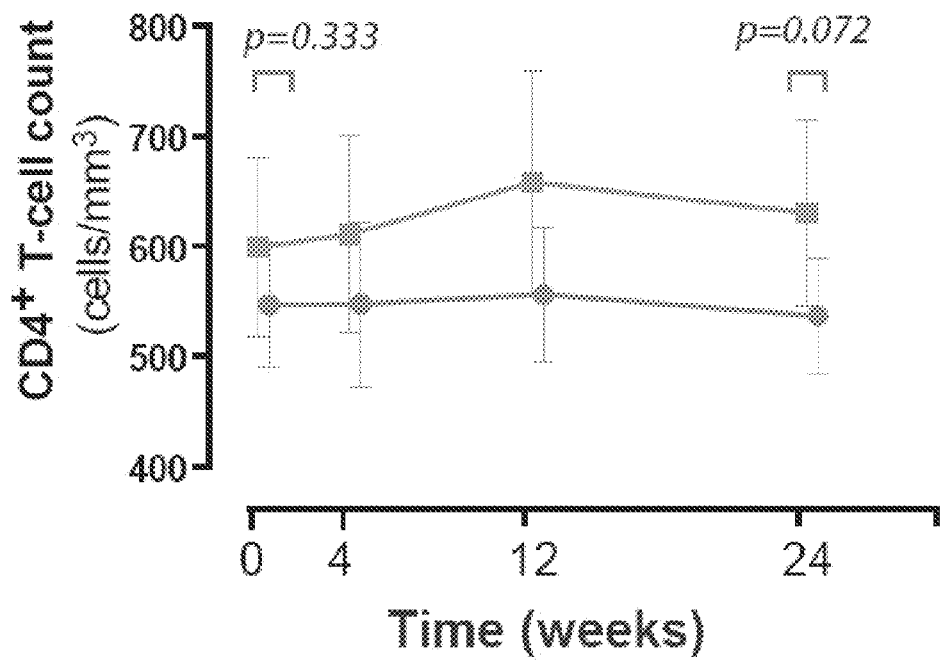
FIGS. 1D-1E are line graphs showing the results of a time course evolution of the CD4+ (1D) and CD8 (1E) T cell counts assessed in fresh blood samples by multicolour flow cytometry at weeks 0, 4, 12 and 24. Filled squares, intensified arm; filled circles, control arm. Mean values±SEM. P values (U Mann Whitney test between groups) are indicated.
Figure 1E:
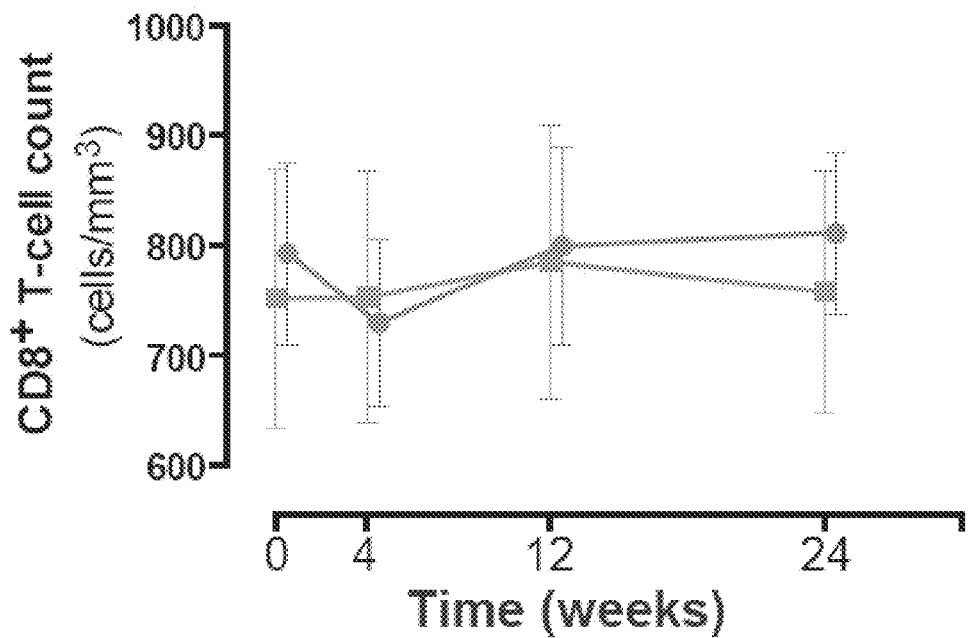
Figure 1F:
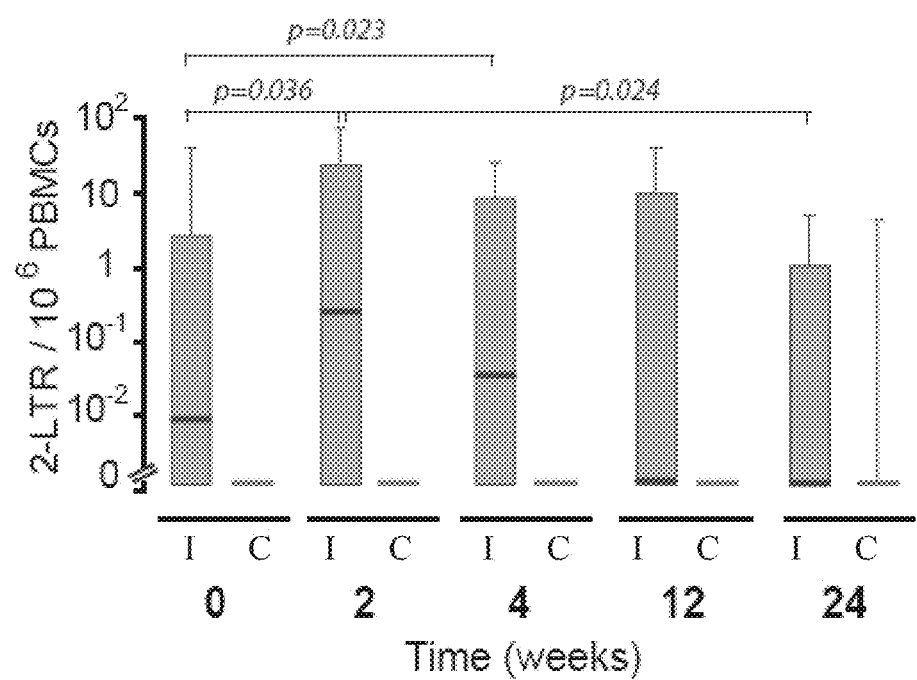
FIG. 1F is a bar graph showing changes in episomal HIV-1 DNA (2-LTR circles) between groups during the study period. Median, 10 and 90 percentiles. I, intensified arm (n=45); c, control arm (n=22). P values (Peto-Prentice-Wilcoxon test, paired data) are indicated.

Both arms had stable CD4+ and CD8+ T cell counts during the study period with only a trend towards an increase in absolute CD4+ T cell counts in the intensification arm respect to the control arm at week 24 (p=0.072, signed rank test, FIG. 1D).

In the formation of 2-LTR circles, U3 and U5 sequences within the 5' and 3' LTRs ligate to form a unique U3-U5 circle junction that is not represented in other forms of viral cDNA (FIG. 1A). Therefore, 2-LTR circles were specifically measured by real-time PCR with primers flanking the 2-LTR circle junction.

HIV-1 DNA purification was isolated as previously described (Hunt et al., J Infect Dis 187, 1534-1543 (2003)) with some modifications. Briefly, a median of 60×10$^6$ PBMCs were purified at weeks 0, 2, 4 and 12 by Ficoll centrifugation and cell pellets were resuspended in 350 ul of P1 buffer (Qiaprep miniprep kit, Qiagen). Then, 250 ul of cell resuspensions were used for extrachromosomal HIV-1 DNA extraction (QIAPREP miniprep kit, Qiagen) using the modification for the isolation of low-copy-number plasmids, and total cellular DNA was purified from 100 ul of cell resuspensions with a standard protocol (QIAAMP DNA Blood Kit, Qiagen).

Real-time PCR-based quantification of HIV-1 2-LTR circles was performed as follows. Extrachromosomal DNA was isolated at weeks 0, 2, 4 and 12 post-intensification. A single-step, real-time PCR was used to quantify 2-LTR circles in a 50 ul PCR reaction mix containing 25 ul of TaqMan® Universal PCR Master Mix (Applied Biosystems), 20 ul of extrachromosomal HIV-1 DNA and primers and probe that span the 2-LTR circle junction. The forward primer was 5' CTA ACT AGG GAA CCC ACT GCT 3' (SEQ ID NO:1) and the reverse primer 5'GTA GTT CTG CCA ATC AGG GAA G 3'(SEQ ID NO:2). The fluorescence taqman probe was 5' AGC CTC AAT AAA GCT TGC CTT GAG TGC 3' (SEQ ID NO:3). Amplification reactions were performed with an Applied Biosystems 7000 Real-time PCR system. The thermocycling conditions were: 95° C. 10 min, 50 cycles at 95° C. 15 sec and 60° C. 1 min, and a final cycle of 72° C. 5 min. Copy number estimates of 2-LTR circles were performed in duplicate and determined by extrapolation from a standard curve generated with a plasmid that harbors the sequence of the 2-LTR junction and CCR5 gene. 2-LTR copy number was calculated relative to CCR5 gene copy number as determined from the chromosomal fraction. Samples corresponding to the same patient were evaluated in the same real time plate to minimize interexperiment variation.

2-LTR circles were detectable in 29% (13/45) of the patients intensified with raltegravir but none (0/22) of the control group at any time point during the study (p=0.003, Fisher's exact test) (FIG. 1B). At baseline 11% (5/43) of the intensified patients showed detectable 2-LTR circles compared to the control arm (0/22) (p=0.132, Pearson's chi square). Within the treatment intensification group there was a significant and transient increase in 2-LTR circles at weeks 2 and 4 compared to baseline (p=0.036 and p=0.023 respectively, Peto-Prentice-Wilcoxon test), and a subsequent decrease afterwards (FIG. 1C). To ascertain if increases in 2-LTR circles were associated with HAART composition, 2-LTR circle-positive patients at any time point of the study were stratified by their background regimen in two groups: those on protease inhibitor or on non-nucleoside reverse transcriptase inhibitor-containing regimens. Increases in 2-LTR circles were mainly observed in patients who intensified their PI-containing regimen (p=0.022, Fisher's exact test).

Total viral DNA forms (comprising unintegrated and integrated viral cDNA) were assayed using internal LTR primers (FIG. 2). Total HIV-1 DNA was amplified from 100% (67/67) of the patients at any time point in the study. Real-time PCR-based quantification of total HIV-1 DNA was performed as follows. Chromosomal DNA was extracted at weeks 0, 2, 4 and 12 after initiation of intensification. A single-step real-time PCR was used to quantify total HIV-1 DNA in a 50 ul PCR reaction mix containing 25 ul of TaqMan® Universal PCR Master Mix (Applied Biosystems), 20 ul of chromosomal HIV-1 DNA and primers and probe that anneal in the 5' and 3' end of the R and U5 region of the LTR respectively, as has previously been described (Brussel and Sonigo, J Virol 77, 10119-10124 (2003)) using a forward primer; 5' GG CTA ACT AGG GAA CCC ACT G 3' (SEQ ID NO:4) and a reverse primer; 5' GCT AGA GAT TTT CCA CAC TGA CTA A 3' (SEQ ID NO:5). The fluorescence taqman probe was 5' GGA TCT CTA GTT ACC AGA GTC A 3' (SEQ ID NO:6). Amplification reactions were performed with an Applied Biosystems 7000 Real-time PCR system. The thermocycling conditions were: 95° C. 10 min, 50 cycles at 95° C. 15 sec and 60° C. 1 min and a final cycle of 72° C. 5 min. Amplification and calculation of copy number was determined as for 2-LTR DNA.

Real-time PCR-based quantification of integrated HIV-1 DNA was performed as follows. Chromosomal DNA was extracted at weeks 0, 2, 4 and 12 after intensification. A two-step real-time PCR was used to quantitate integrated HIV-1 DNA using Alu-LTR primers as has previously been described (Brussel and Sonigo, J Virol 77, 10119-10124 (2003)). Briefly, in the first round of PCR only 12 cycles of amplification was performed, integrated HIV-1 sequences were amplified with two outward-facing Alu primers together with an HIV-1 LTR specific primer extended with a lambda phage-specific heel sequence in a 20 ul reaction mixture. In a second round of PCR, a lambda specific primer and an LTR primer was used on 1/10th of the first-round PCR product in a 50 ul mixture PCR reaction. The forward primer was 5' ATG CCA CGT AAG CGA AAC T 3' (SEQ ID NO:7) and the reverse primer 5'GCT AGA GAT TTT CCA CAC TGA CTA A 3' (SEQ ID NO:8). The fluorescence taqman probe was 5'GGA TCT CTA GTT ACC AGA GTC A 3' (SEQ ID NO:9).

Figure 2A:
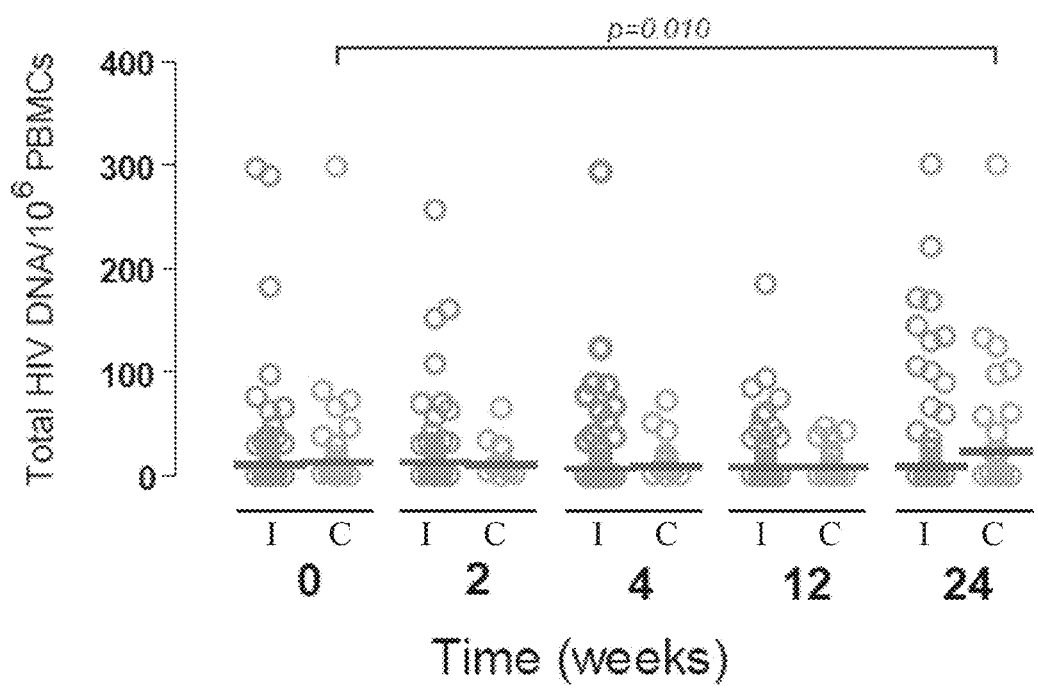
FIGS. 2A and 2B is a dot graph showing changes in total (2A) and integrated (2B) HIV-1 DNA during 12 weeks of intensification. Chromosomal DNA was extracted from $60 \times 10^6$ PBMCs at weeks 0, 2, 4 and 12 after initiation of the study and Real-Time PCR used to quantitate different forms of HIV-1 cDNA. I, intensified arm; C, control arm.
Figure 2B:
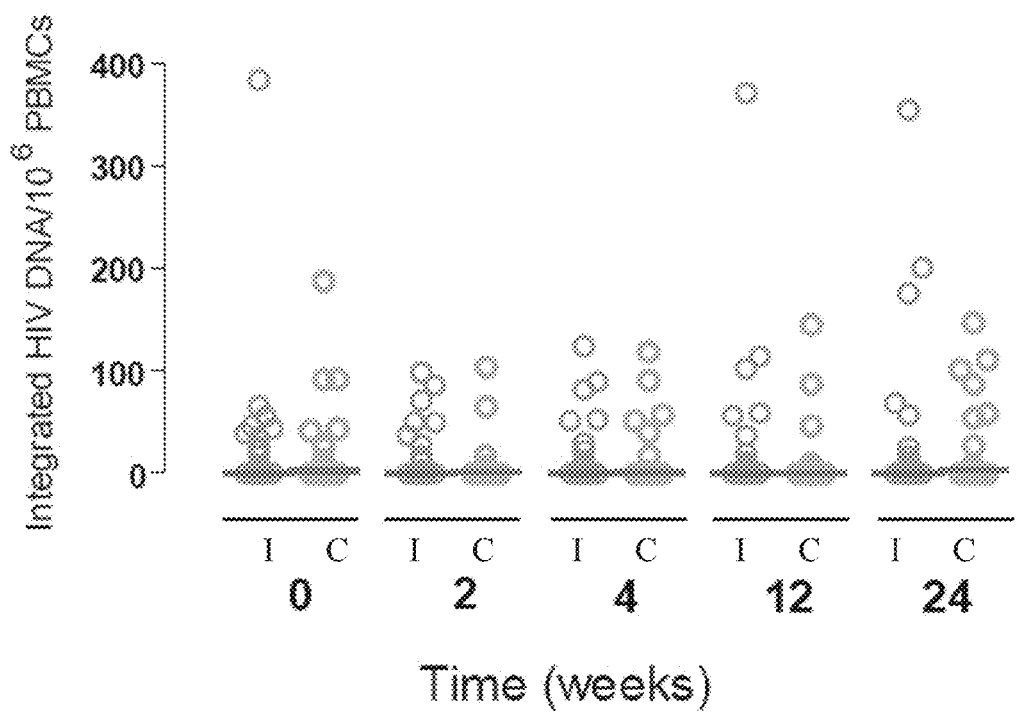
Figure 2C:
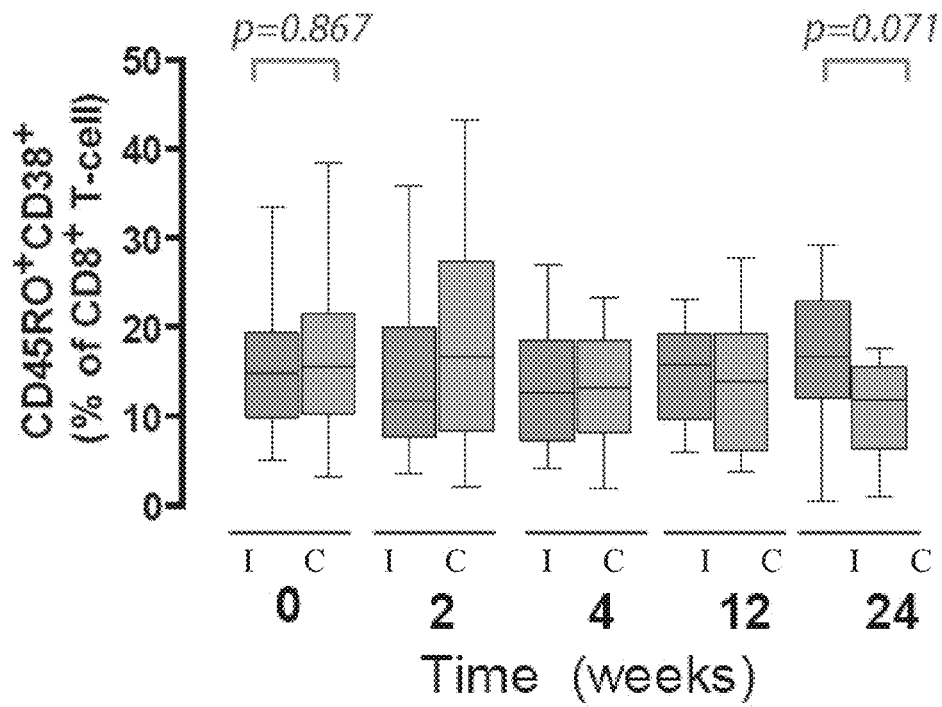
FIGS. 2C-2F are box-whisker plots showing the results of phenotypic analysis of lymphocytes subsets in intensified and control arms was assessed in fresh blood samples by multi-colour flow cytometry at weeks 0, 2, 4, 12 and 24. (2C) The CD4+ T cell memory, measured as the percentage of CD4+CD45RA-. (2D) The CD8+ T cell activation, measured as the percentage of CD8+CD45RO+CD38+. (2E) The CD8+ T cell activation, measured as the percentage of CD8+HLADR+CD45RO+. (2F) The CD8+ T cell activation, measured as the percentage of CD8+HLA-DR+CD38+. Median, 25 and 75 percentiles. I, intensified arm; C, control arm. P values (U Mann Whitney test between groups; and signed rank test, paired data, within groups) are indicated.
Figure 2D:
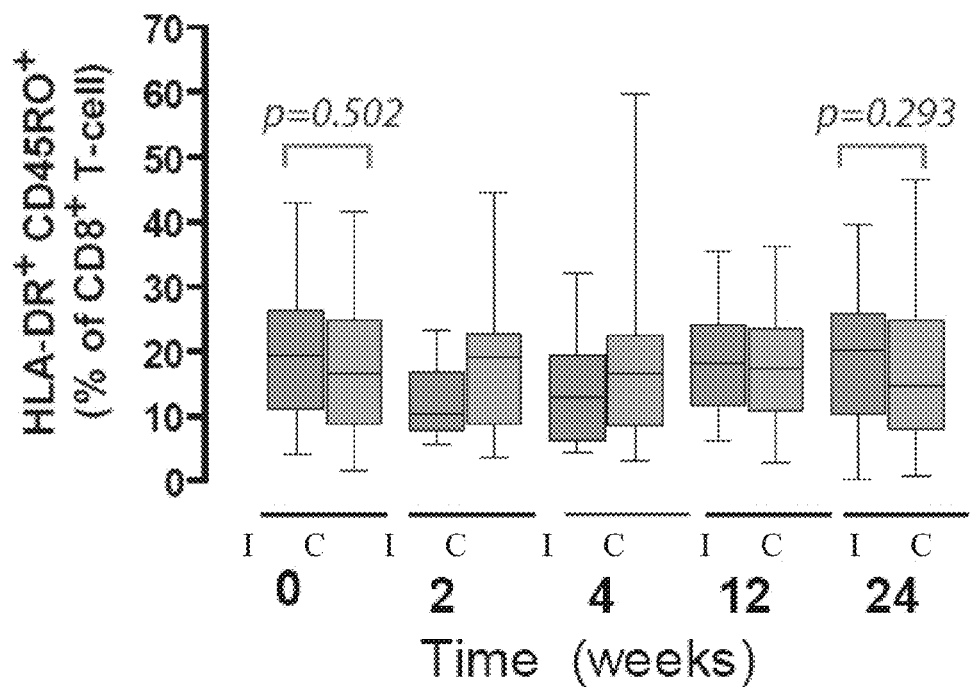
Figure 2E:
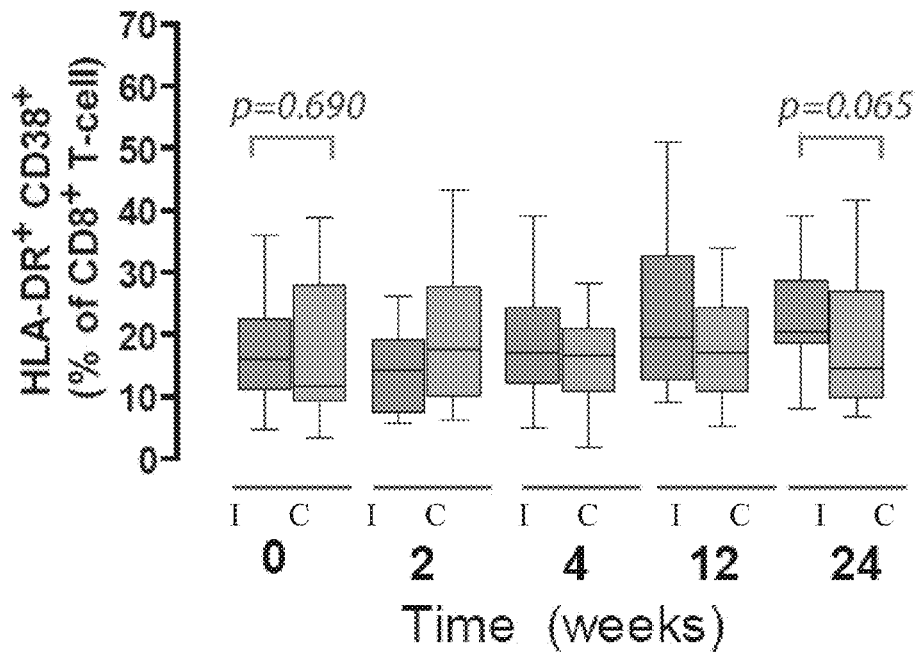
Figure 2F:
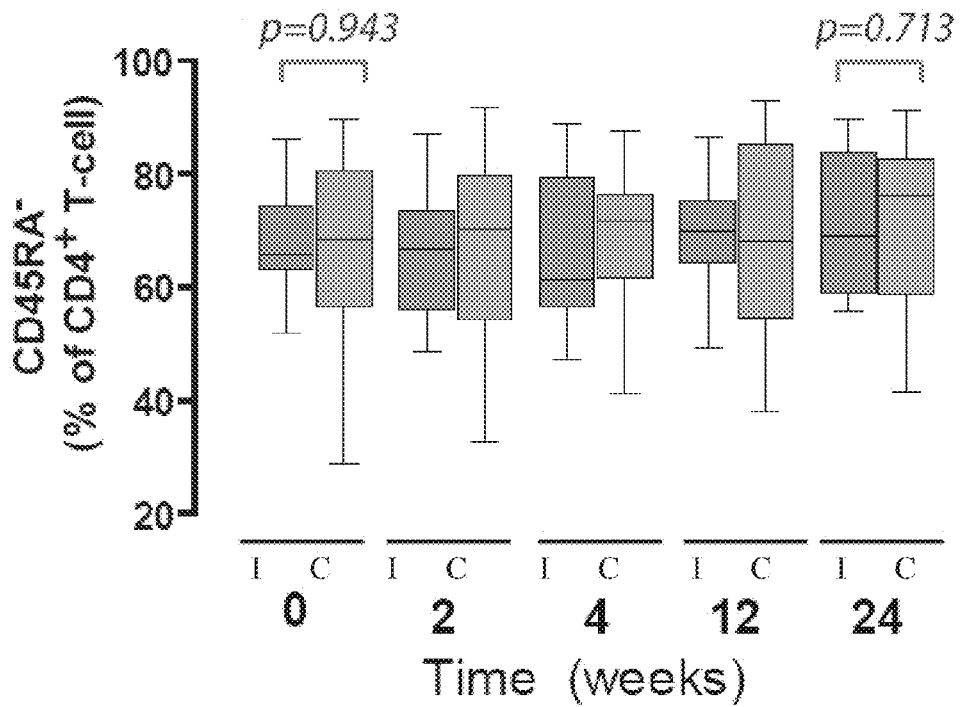

Amplification and calculation of copy number was determined as for 2-LTR DNA. No longitudinal changes were observed in total HIV-1 DNA in any of the groups during the study period (control arm: p=0.987; intensification arm: p=0.342, signed rank test). Moreover, no differences were observed between groups at any time point (FIG. 2A). Integrated proviral DNA was measured using LTR-Alu primers. Integrated HIV-1 DNA was amplified from 87% (39/45) of the intensified patients and from 86% (19/22) of the patients randomized to the control arm at any time point after initiation of the study (p=0.252, Pearson's chi square). No longitudinal changes were observed in integrated HIV-1 DNA in any of the groups during the study period (control arm: p=0.252; intensification arm: p=0.768, signed rank test) and no differences were observed between groups at any time interval (FIG. 2B). Of note, we found a longitudinal correlation between total and integrated HIV-1 DNA (control arm: rho=0.45; intensification arm: rho=0.42, p<0.001). Overall, despite the effect of raltegravir on 2-LTR circles in the intensified group, the levels of total and integrated HIV-1 DNA remained stable throughout the 12 weeks of intensification.

Immune hyperactivation is a hallmark of pathogenic lentivirus infection (Brenchley et al., Nat Med 12, 1365-1371 (2006)) causing increased levels of proliferation and apoptosis. Suppressive HAART reduces the level of immune activation in HIV-1-infected patients (Kolber et al., Clin Immunol 126, 315-321 (2008)) but does not normalize it (Hunt et al., J Infect Dis 187, 1534-1543 (2003)). Higher levels of immune activation and plasma lipopolysaccaride are also associated with impaired immune restoration in HAART (Jiang et al., supra). However, a causative link between active viral replication and immune activation has not been established. In the raltegravir-intensified and control groups, there was no major changes in memory CD4+ or activated CD8+ T cells throughout the study period (Table 1, FIGS. 2C-F), although an slight increase in the percentage of CD8+HLA-DR+CD38+ cells in the control arm was observed after 24 weeks (p=0.041). Therefore, we examined whether immune activation levels might be higher in those patients who had detectable 2-LTRs (2-LTR+) at any time point of the study (n=13) relative to those in which 2-LTRs were undetectable (2-LTR−) (n=32).

Analysis of lymphocyte subsets and immune activation was performed as follows. A total of 52 patients, 34 in the intensification group and 18 patients in the control group, had fresh blood samples available for flow cytometry analysis through the study period. Different combinations of antibodies were used to characterize different lymphocyte subsets: combination 1 was designed to evaluate naïve/memory subsets and contained CD45RA-FITC, CD31-PE, CD38-PerCP, CD3-APC-Cy7, CD4-APC and CD8-PE-Cy7; combination 2 was designed to evaluate the activation of CD8 T cells and contained HLA-DR-FITC, PD-1-PE, CD38-PerCP, CD45RO-APC, CD3-APC-Cy7 and CD8-PE-Cy7. Controls with combinations of CD3-APC-Cy7, CD4-APC and CD8-PE-Cy7 antibodies were performed for all samples. All antibodies were obtained from Becton Dickinson. Briefly, 20 ul of fresh whole blood was incubated with antibodies for 15 min at room temperature with the different antibody combinations in V-bottom 96-well plates. Red cells were lysed using the BD FACs lysing solution (Becton Dickinson), washed once with PBS and resuspended in PBS containing 1% formaldehyde. Acquisition of flow cytometry data was performed on an LSRII flow cytometer (Becton Dickinson) coupled with a HTS loader. At least 30,000 lymphocytes were collected for each sample. Analyses were performed with FlowJo software (Tree Star Inc.).

Figure 3A:
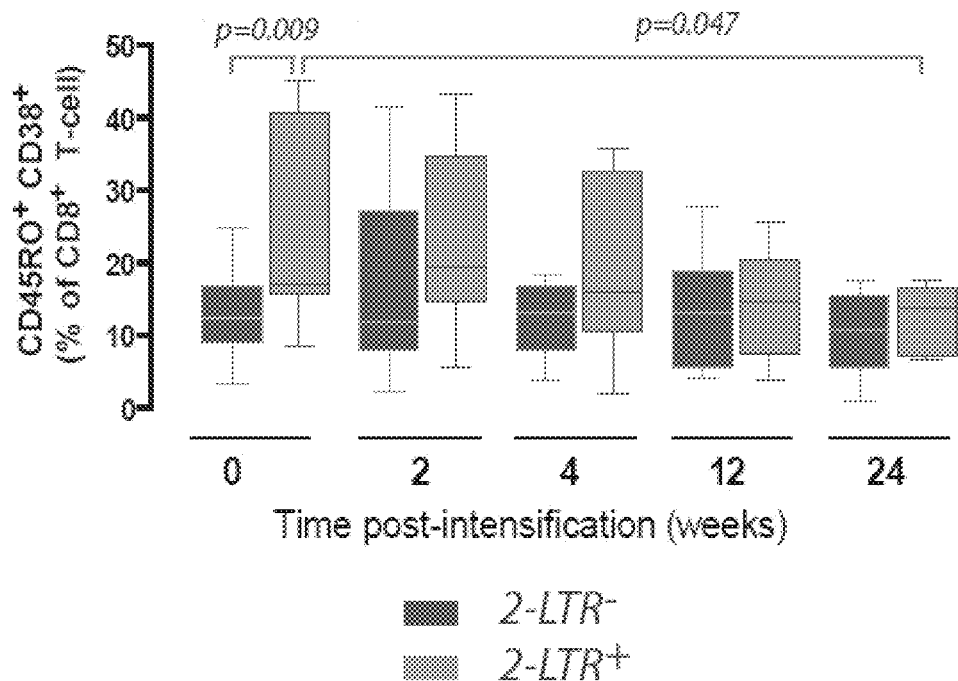
FIGS. 3A-3B are box-whisker plots showing the results of phenotypic analysis of lymphocytes subsets in intensified after stratification on the basis of 2-LTR positivity (2-LTR+) and negativity (2-LTR-) was assessed in fresh blood samples by multicolour flow cytometry at weeks 0, 2, 4, 12 and 24. (3A) Time course of the CD8+ T cell activation, measured as the percentage of CD8+CD45RO+CD38+, and (3B) the CD4+ T cell memory, measured as the percentage of CD4+CD45RA-. Median, 25 and 75 percentiles. Light grey boxes represent the 2-LTR+ group while the 2-LTR- group is represented by dark grey boxes. P values (U Mann Whitney test between groups; and signed rank test, paired data, within groups) are indicated.
Figure 3B:
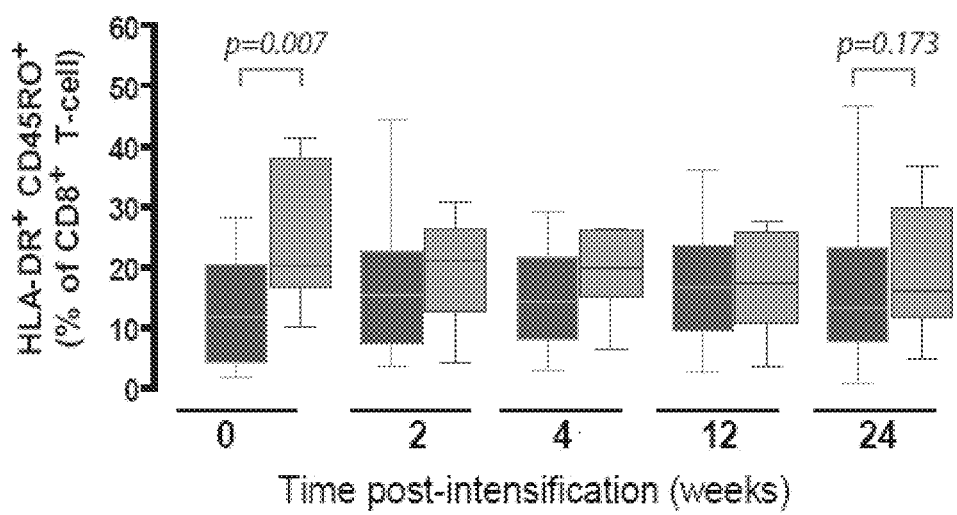
Figure 3C:
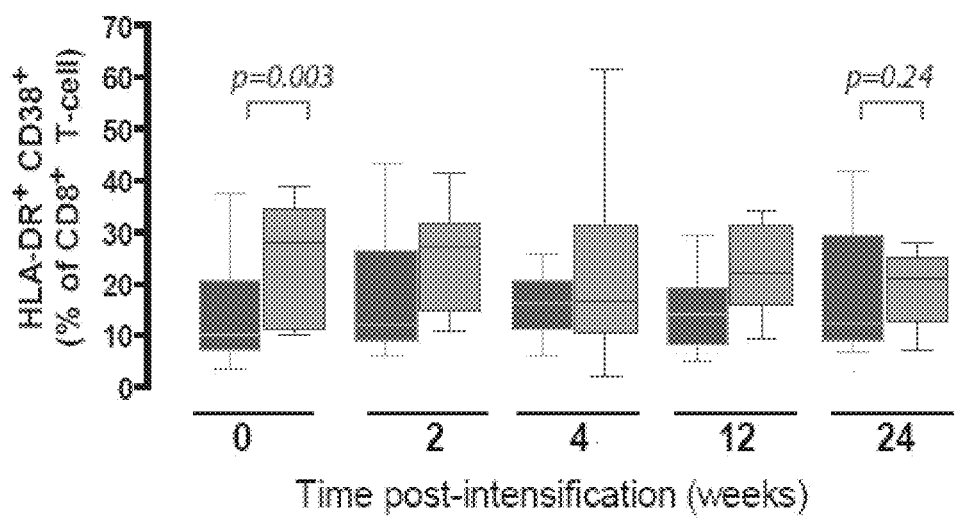
FIGS. 3C-3D are box-whisker plots showing the results of phenotypic analysis of lymphocytes subsets in intensified after stratification on the basis of 2-LTR positivity (2-LTR+) and negativity (2-LTR-) was assessed in fresh blood samples by multicolour flow cytometry at weeks 0, 2, 4, 12 and 24. (3C) Time course evolution of the CD8+ T cell activation, measured as the percentage of CD8+HLA-DR+CD45RO+, and (3D) the CD8+ T cell activation, measured as the percentage of CD8+HLADR+CD38+. Median, 25 and 75 percentiles. Light grey boxes represent the 2-LTR+ group while the 2-LTR- group is represented by dark grey boxes. P values (U Mann Whitney test between groups; and signed rank test, paired data, within groups) are indicated.
Figure 3D:
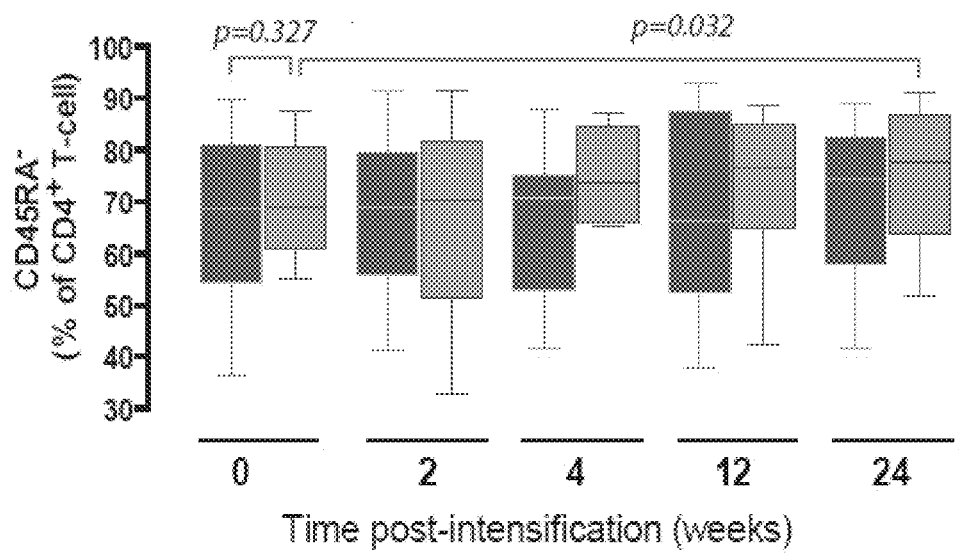

At baseline, the 2-LTR+ group exhibited higher percentages of activated CD8+ T cells when compared with 2-LTR− patients: CD8+CD45RO+CD38+ (p=0.0092; FIG. 3A), CD8+HLA-DR+CD45RO+ (p=0.0066; FIG. 3C), and CD8+HLA-DR+CD38+ (p=0.0029; FIG. 3D). However, no differences were observed in memory CD4+ cells (CD4+CD45RA−) at baseline between the 2-LTR+ and 2-LTR− groups (p=0.327; FIG. 3B). In the control group, where no selection by 2-LTR status was possible, intermediate levels of all parameters were apparent in all cases. There was no correlation between total or integrated HIV-1 DNA and immune activation parameters at baseline. In longitudinal analysis, there was a significant reduction of CD8+ T cell activation markers in the intensified group that was particularly evident in activated memory CD8+ T cells (CD8+CD45RO+CD38+, p=0.0469, FIG. 3A) while the other two markers of activated CD8+ T cells (CD8+HLA-DR+CD45RO+ and CD8+HLA-DR+CD38+) lost the initial baseline difference between the 2-LTR+ and the 2-LTR− groups after 24-weeks of intensification (FIGS. 3C-D). There was also a trend toward a greater increase in absolute CD4+ T cell counts among groups (p=0.085; signed rank test, data not shown), with a higher increase in the percentage of memory CD4+ T cells in the 2-LTR+ group (CD4+CD45RA−; p=0.032, FIG. 3B).

Statistical analysis for the above-described experiments was performed as follows. To compare at each time point medians of total and integrated HIV-1 DNA, absolute lymphocyte counts and relative percentages between the control and intensification arm (or between patients classified as 2-LTR+ and 2-LTR−) the U Mann Whitney test was used. In each group longitudinal changes of total and integrated HIV-1 and immune activation parameters were assessed through the signed rank test (paired test) comparing weeks 0 and 12, or weeks 0 and 24 respectively. Differences in proportions between groups were analyzed through the Pearson's chi square, considering the continuity correction or the Fisher's exact test, as appropriate. Within the intensified arm, differences in 2-LTR circles at weeks 2 and 4 compared to baseline were analyzed using Peto-Prentice-Wilcoxon test. Correlation between total or integrated HIV-1 DNA and immune activation parameters was computed with the Spearman's rho coefficient. Values of p<0.05 indicated statistical significance. Statistical analyses were performed with SAS® 9.1 software and graphics were generated with GraphPad® Prism 5.0 software.

As demonstrated herein, raltegravir intensification revealed the presence of active replication in a significant percentage (29%) of patients on suppressive HAART. Raltegravir specifically prevents integration of linear viral cDNA to promote an increase in episomal cDNA formation. Since linear cDNA is a product of reverse transcription during active infection, the increase in episomal cDNA following raltegravir intensification requires the presence of infectious virus and also requires de novo infection and reverse transcription: which together, strongly suggest that active viral replication persists in HAART. The fact that the increase in episomal cDNA was transient further suggests that raltegravir effectively blocked active replication and production of infectious virions. However, other factors such as CTL targeting of cells containing transcriptionally active episomal HIV-1 cDNA, action of cell nucleases or a 2-LTR dilution effect due to cell proliferation might also play a role. Raltegravir intensification did not cause significant fluctuations in the levels of total or integrated viral cDNA. This is in agreement with our previous observations that in contrast to episomal cDNA, the majority of proviral DNA is archival and non-dynamic (Sharkey et al., J Virol 79, 5203-5210 (2005)).

The increase in 2-LTR circles was observed mainly in those intensified patients on a PI-containing regimen. It is possible that the presence of three reverse transcriptase inhibitors in the non-PI-containing regimens may reduce the probability for formation of the linear cDNA precursor to episomal cDNA. It is also possible that active replication occurs in an anatomic compartment that is less accessible to PIs. Furthermore, an inability to detect episomal cDNA in about 70% of the patients in this study suggests that current HAART regimens can effectively suppress active replication in the majority of patients. This would be concordant with previous studies where there was no evidence for evolutionary changes within the viral sequences in patients on HAART (Bailey et al., (2006) supra; Kieffer et al. (2004) supra; Parera et al. (2004) supra).

This study also reveals a causative relationship between active replication and immune activation. The observed normalization of immune activation in those patients in which raltegravir impacted active replication (as evidenced by an increase in 2-LTRs) suggests that in HAART, active replication is a cause of aberrant immune activation rather than a consequence of it. The extent of immune activation as well as plasma LPS levels are predictive of poor CD4 cell reconstitution in HAART (Jiang et al., supra). Therefore, while active replication might occur at a low level in HAART, it is likely to significantly impact the ability of HAART to restore T cell homeostasis.

This study raises the question as to what extent does active replication contribute to viral persistence in HAART. For example, the longevity of the latent reservoir may, in part, be attributable to continual replenishment by virus produced by active replication. It could be argued that, in the presence of HAART, there is not a complete life cycle within individual, infected cells (i.e., a cell gets infected but does not make particles) and that the infectious particles are being made by a chronically infected cell that is simply manufacturing virions. However, even in this scenario, conditions would exist for sequence evolution and for viral reservoir replenishment. Therefore, intensification regimens that prevent active replication may truncate this replenishment and accelerate the decay of the reservoirs that persist in HAART.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of detecting the presence of replication competent human immunodeficiency virus 1 (HIV-1) virus in a subject who is being treated with an intensified highly active anti-retroviral therapy (HAART) regimen, the method comprising:
   selecting a subject who is being treated with an intensified HAART regimen including an integration inhibitor;
   obtaining a sample comprising blood;
   specifically amplifying a segment spanning two-long terminal repeat (2-LTR) junction of 2-LTR circles using polymerase chain reaction (PCR) to determine a level of 2-LTR circles in the sample; and
   determining the presence of replication competent HIV-1 virus based on the level of 2-LTR circles in the sample.

2. The method of claim 1, further comprising determining that the subject has no detectable plasma levels of viral RNA.

3. The method of claim 2, comprising determining that the subject has fewer than about 50 copies/ml plasma of viral RNA.

4. The method of claim 1, wherein the sample comprises peripheral blood mononuclear cells (PBMCs).

5. The method of claim 1, wherein the integration inhibitor is raltegravir or elvitegravir.

6. The method of claim 1, wherein the intensified HAART regimen also includes a protease inhibitor.

7. A method of monitoring an intensified HAART regimen in a subject infected with HIV-1, the method comprising:
   selecting a subject who is being treated with an intensified HAART regimen including an integration inhibitor;
   obtaining a first sample comprising blood from the subject;
   determining a first level of 2-LTR circles in the first sample by specifically amplifying a segment spanning 2-LTR junction of 2-LTR circles using PCR;
   obtaining a second sample comprising blood from the same subject at least one month after obtaining the first sample;
   determining a second level of 2-LTR circles in the second sample by specifically amplifying a segment spanning 2-LTR junction of 2-LTR circles using PCR; and
   comparing the second level with the first level of 2-LTR circles,
   determining that the intensified HAART regimen is effective when there is a decrease in the second level of 2-LTR circles, or ineffective when there is no change or an increase in the second level of 2-LTR circles, when compared with the first level of 2-LTR circles.

8. The method of claim 7, wherein the second sample is obtained at least six months after obtaining the first sample.

9. The method of claim 7, wherein the integration inhibitor is raltegravir or elvitegravir.

10. The method of claim 7, wherein the sample comprises peripheral blood mononuclear cells (PBMCs).

11. The method of claim 7, further comprising determining that the subject has no detectable plasma levels of viral RNA.

12. The method of claim 9, comprising determining that the subject has fewer than 50 copies/ml plasma of viral RNA.

13. A method of determining the effectiveness of an intensification agent for a subject who is being treated with standard HAART for HIV-1 infection, the method comprising:
   selecting a subject who is being treated with standard HAART;
   obtaining a first sample comprising blood from the subject;
   determining a baseline level of 2-LTR circles in the first sample by specifically amplifying a segment spanning 2-LTR junction of 2-LTR circles using PCR;
   adding an intensification agent comprising an integration inhibitor to the standard HAART treatment;
   obtaining a second sample comprising blood from the subject at two weeks after addition of the intensification agent;
   determining a treatment level of 2-LTR circles in the second sample by specifically amplifying a segment spanning 2-LTR junction of 2-LTR circles using PCR;
   comparing the treatment level with the baseline level of 2-LTR circles; and
   determining that the intensification agent is effective when the treatment level of 2-LTR circles determined at two weeks after addition of the intensification agent is greater than the baseline level.

14. The method of claim 13, wherein the integration inhibitor is raltegravir or elvitegravir.

15. The method of claim 13, wherein the sample comprises peripheral blood mononuclear cells (PBMCs).

16. The method of claim 13, further comprising determining that the subject has no detectable plasma levels of viral RNA.

17. A method of determining the effectiveness of an intensification agent for a subject who is being treated with standard HAART for HIV-1 infection, the method comprising:
   selecting a subject who is being treated with standard HAART;
   obtaining a first sample comprising blood from the subject;
   determining a baseline level of 2-LTR circles in the first sample by specifically amplifying a segment spanning 2-LTR junction of 2-LTR circles using PCR;
   adding an intensification agent comprising an integration inhibitor to the standard HAART treatment;
   obtaining a second sample comprising blood from the subject at six months after addition of the intensification agent;
   determining a treatment level of 2-LTR circles in the second sample by specifically amplifying a segment spanning 2-LTR junction of 2-LTR circles using PCR;
   comparing the treatment level with the baseline level of 2-LTR circles; and
   determining that the intensification agent is effective when the treatment level of 2-LTR circles determined at six months after addition of the intensification agent is lower than the baseline level.

18. The method of claim 17, wherein the integration inhibitor is raltegravir or elvitegravir.

19. The method of claim 17, wherein the sample comprises peripheral blood mononuclear cells (PBMCs).

20. The method of claim 17, further comprising determining that the subject has no detectable plasma levels of viral RNA.

* * * * *

UNITED STATES PATENT AND TRADEMARK OFFICE
CERTIFICATE OF CORRECTION

| | | Page 1 of 1 |
|---|---|---|
| PATENT NO. | : 8,748,088 B2 | |
| APPLICATION NO. | : 13/145307 | |
| DATED | : June 10, 2014 | |
| INVENTOR(S) | : Mario Stevenson | |

It is certified that error appears in the above-identified patent and that said Letters Patent is hereby corrected as shown below:

Title page: Item (54), and in the Specification, Column 1, line 3, delete "RECEIVEING" and insert -- RECEIVING --.

Title page: Item (56), line 12, delete "immunodefiicencyvirus" and insert -- immunodeficiency virus --.

IN THE SPECIFICATION:

Column 1, before line 7, insert the following paragraph

-- STATEMENT OF FEDERALLY SPONSORED RESEARCH

This invention was made with government support under grant nos. AI032391, RR011589, HL057880 and AI032907 awarded by the National Institutes of Health. The government has certain rights in the invention. --.

IN THE CLAIMS:

Column 17, line 56, Claim 12, delete "9" and insert -- 7 --.

Signed and Sealed this
Twenty-third Day of December, 2014

Michelle K. Lee
*Deputy Director of the United States Patent and Trademark Office*

SEQUENCE LISTING

```
<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
ctaactaggg aacccactgc t                                              21

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
gtagttctgc caatcaggga ag                                             22

<210> SEQ ID NO 3
<211> LENGTH: 27
<212> TYPE: DNA
<213> ORGANISM: Artificial Sequence
<220> FEATURE:
<223> OTHER INFORMATION: Primer
```

```
<400> SEQUENCE: 3
agcctcaata aagcttgcct tgagtgc                                        27

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
ggctaactag ggaacccact g                                              21

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
ggctaactag ggaacccact g                                              21

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
ggatctctag ttaccagagt ca                                             22

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
atgccacgta agcgaaact                                                 19

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
gctagagatt ttccacactg actaa                                          25

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
ggatctctag ttaccagagt ca                                             22
```